US009958366B2

United States Patent
Surowiec et al.

(10) Patent No.: US 9,958,366 B2
(45) Date of Patent: May 1, 2018

(54) STONE IMPACT SIMULATOR

(71) Applicant: FORD GLOBAL TECHNOLOGIES, LLC, Dearborn, MI (US)

(72) Inventors: Roman Surowiec, Redford, MI (US); Edward J. Stadler, Jr., Dearborn, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 263 days.

(21) Appl. No.: 15/052,147

(22) Filed: Feb. 24, 2016

(65) Prior Publication Data

US 2017/0241880 A1 Aug. 24, 2017

(51) Int. Cl.
*G01N 3/307* (2006.01)
(52) U.S. Cl.
CPC .................... *G01N 3/307* (2013.01)
(58) Field of Classification Search
CPC ................... G01N 3/30; G01N 3/307
See application file for complete search history.

(56) References Cited

U.S. PATENT DOCUMENTS

| | | | | |
|---|---|---|---|---|
| 2,517,545 A * | 8/1950 | Cushman | ................ | G01N 3/30 124/6 |
| 2,905,321 A * | 9/1959 | Hitchner | ................ | G01N 3/30 209/699 |
| 3,793,874 A * | 2/1974 | Shockey | ................ | G01N 3/307 73/12.11 |
| 3,896,657 A * | 7/1975 | Brandt | ................ | G01N 3/307 73/12.11 |
| 4,270,383 A * | 6/1981 | Singer | ................ | G01N 3/307 73/82 |
| 5,024,091 A * | 6/1991 | Pellerin | ................ | G01N 3/30 73/597 |
| 5,036,696 A * | 8/1991 | Ahrens | ................ | G01N 3/307 73/12.11 |
| 5,165,270 A * | 11/1992 | Sansalone | ................ | G01N 3/30 73/12.08 |
| 5,739,411 A * | 4/1998 | Lee | ................ | G01N 3/48 73/12.09 |

(Continued)

FOREIGN PATENT DOCUMENTS

| | | |
|---|---|---|
| CN | 2795841 Y | 7/2006 |
| CN | 101672724 A | 3/2010 |

(Continued)

OTHER PUBLICATIONS

English Machine Translation of CN101672724A.

(Continued)

*Primary Examiner* — David Bolduc
(74) *Attorney, Agent, or Firm* — Jason Rogers; King & Schickli, PLLC

(57) ABSTRACT

A stone impact simulator is provided. That stone impact simulator includes a projectile propulsion section to propel a projectile toward a test sample and a projectile capture section to capture the projectile after the projectile ricochets off of the test sample. The projectile capture section includes a rebound block, a spent projectile storage compartment and a projectile energy dissipation element between the rebound block and the spent projectile storage compartment.

20 Claims, 3 Drawing Sheets

(56) References Cited

U.S. PATENT DOCUMENTS

| | | | | |
|---|---|---|---|---|
| 8,408,042 | B2* | 4/2013 | Perrier | G01M 7/08 |
| | | | | 73/12.01 |
| 8,935,963 | B2* | 1/2015 | Bartyczak | G01N 3/307 |
| | | | | 73/756 |
| 9,719,901 | B2* | 8/2017 | Jackson | G01N 3/307 |
| 2006/0032288 | A1* | 2/2006 | Correia | G01N 3/48 |
| | | | | 73/12.11 |
| 2009/0113987 | A1* | 5/2009 | Kaneko | G01N 3/30 |
| | | | | 73/12.05 |
| 2014/0305187 | A1* | 10/2014 | Beran | G01M 17/0078 |
| | | | | 73/12.07 |

FOREIGN PATENT DOCUMENTS

| | | |
|---|---|---|
| CN | 101694446 B | 5/2011 |
| CN | 104865142 A | 8/2015 |
| CN | 104913891 A | 9/2015 |
| JP | 2006047131 A | 2/2006 |
| KR | 101267792 B1 | 6/2013 |

OTHER PUBLICATIONS

English Machine Translation of CN101694446B.
English Machine Translation of CN104865142A.
English Machine Translation of CN104913891A.
English Machine Translation of CN2795841Y.
English Machine Translation of JP2006047131A.
English Machine Translation of KR101267792B1.
Prior Art Stone Impact Simulator from 1990s.

* cited by examiner

STONE IMPACT SIMULATOR

TECHNICAL FIELD

This document relates generally to the field of product testing devices and, more particularly, to a stone impact simulator for testing the impact resistance of a test sample such as a windshield for a motor vehicle.

BACKGROUND

It is known in the art of product testing devices to provide a stone impact simulator for testing the impact resistance of a test sample. This is done by discharging a projectile, of known size, shape and weight, at a given angle to impact the test sample with a known velocity.

This document relates to a new and improved stone impact simulator that is quieter in operation and less self-destructive so as to provide a longer service life than such devices found in the prior art.

SUMMARY

In accordance with the purposes and benefits described herein, a stone impact simulator is provided. That stone impact simulator comprises a projectile propulsion section to propel a projectile toward a test sample and a projectile capture section to safely capture the projectile after ricocheting off the test sample. The projectile capture section includes a rebound block, a spent projectile storage compartment and a projectile energy dissipation element between the rebound block and the spent projectile storage compartment.

The projectile energy dissipation element may include a frustoconical wall. That frustoconical wall may have a cone angle of between 5 degrees and 20 degrees. In another embodiment, the frustoconical wall has a cone angle of about 15 degrees.

The rebound block may have an arcuate face. That arcuate face may have a radius of curvature of between 1 and 3 inches. In one possible embodiment, that arcuate face has a radius of curvature of between 2.3 and 2.5 inches. In yet another possible embodiment, that arcuate face has a radius of curvature of about 2.41 inches.

The projectile capture section may further include a curved ramp between the rebound block and the projectile energy dissipation element. That curved ramp may include a shallow, arcuate channel. That arcuate channel may have a radius of curvature of between 0.25 and 0.50 inches.

The projectile propulsion section may include a barrel to guide and accelerate the projectile toward the test sample. The stone impact simulator may further include a speed trap between the barrel and the test sample. In addition, the stone impact simulator may include a housing for holding the projectile propulsion section and the projectile capture section. That housing may include a support for resting the housing against the test sample with the barrel at an angle of between about 10 to 75 degrees with respect to the test sample. Further, the housing may be inclined at a similar angle with respect to a horizontal line with the test sample oriented in a vertical plane.

Still further, the barrel and the speed trap are aligned along a first axis while the rebound block, the curved ramp, the projectile energy dissipation element and the spent projectile storage compartment are aligned along a second axis. The first axis may be parallel to the second axis. Further, the first axis and the second axis may be inclined at an angle of about 45 degrees with respect to a horizontal line when the stone impact simulator is in use.

In the following description, there are shown and described several preferred embodiments of the stone impact simulator. As it should be realized, the stone impact simulator is capable of other, different embodiments and its several details are capable of modification in various, obvious aspects all without departing from the stone impact simulator as set forth and described in the following claims. Accordingly, the drawings and descriptions should be regarded as illustrative in nature and not as restrictive.

BRIEF DESCRIPTION OF THE DRAWING FIGURES

The accompanying drawing figures incorporated herein and forming a part of the specification, illustrate several aspects of the stone impact simulator and together with the description serve to explain certain principles thereof. In the drawing figures.

Reference will now be made in detail to the present preferred embodiments of the stone impact simulator, examples of which are illustrated in the accompanying drawing figures.

DETAILED DESCRIPTION

Figure 1:
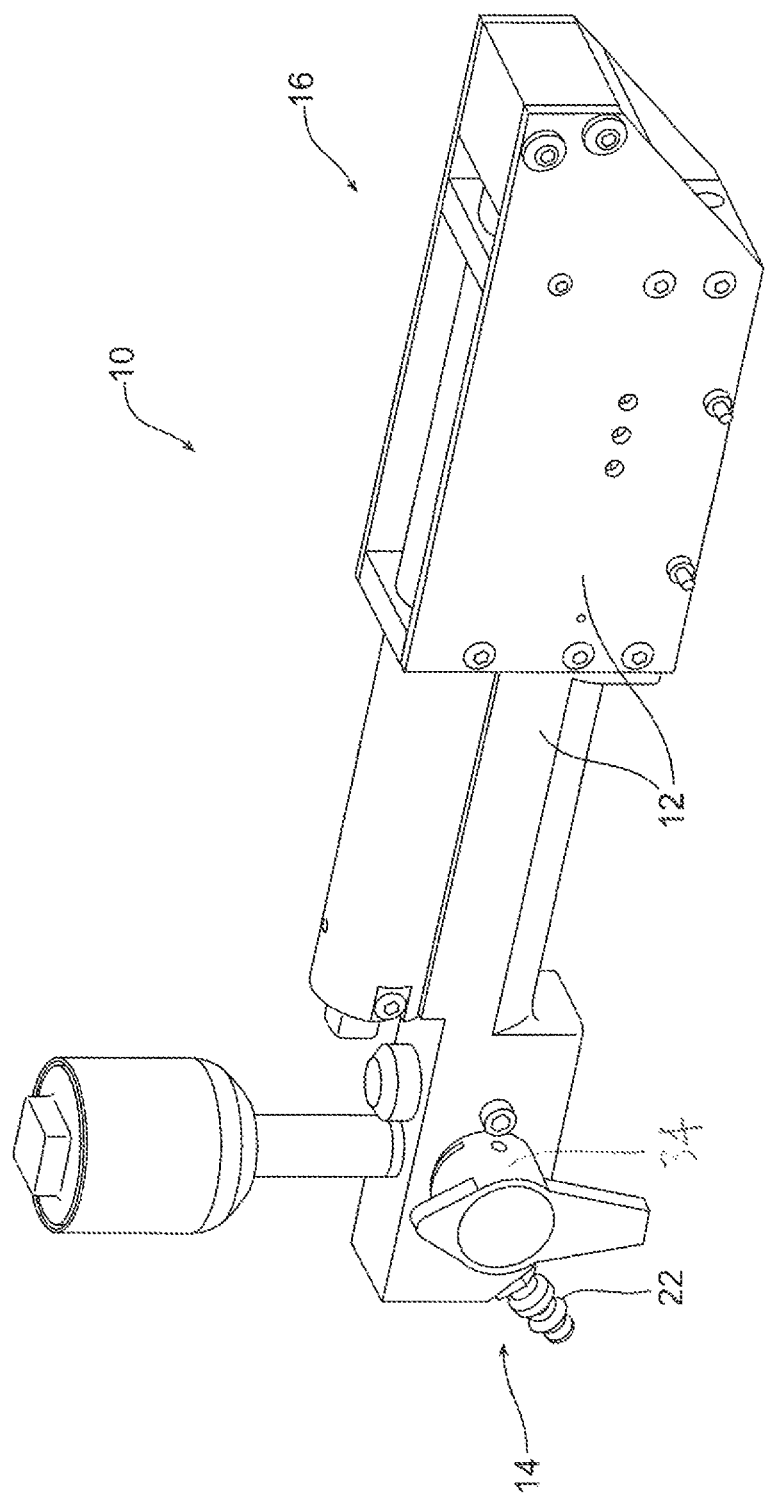
FIG. 1 is a perspective view of the stone impact simulator.
Figure 2:
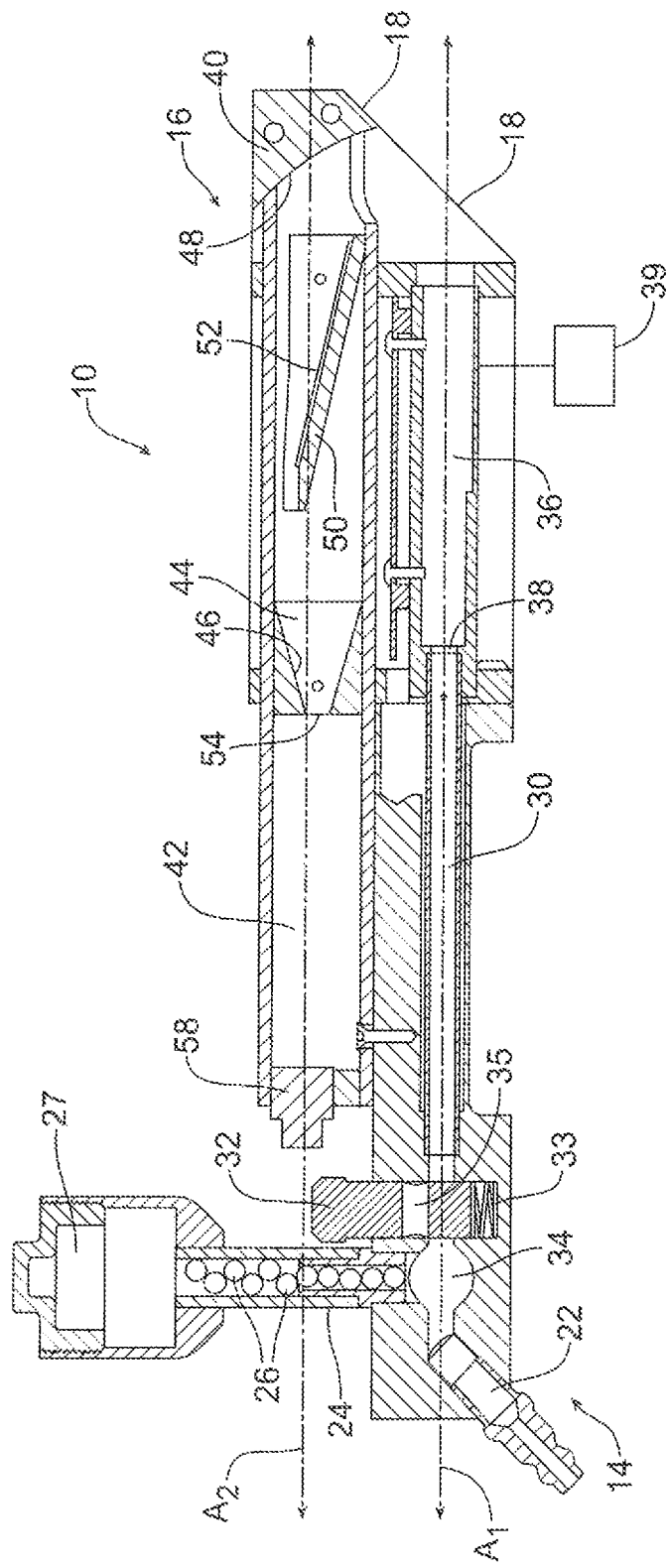
FIG. 2 is a cross sectional view of the stone impact simulator illustrated in FIG. 1.
Figure 3:
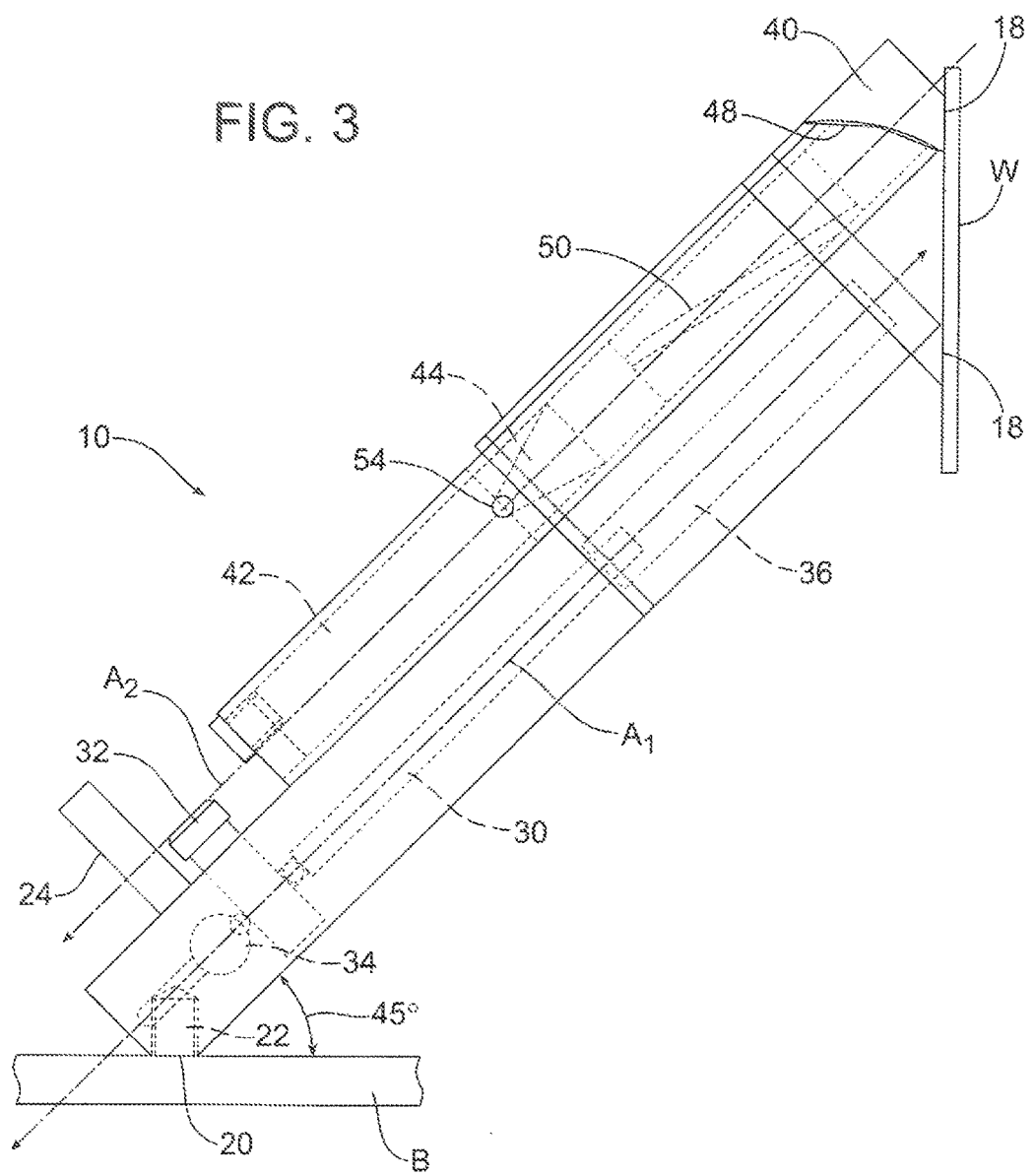
FIG. 3 is a schematic side elevational view of the stone impact simulator illustrating its orientation at approximately a 45 degree angle between the horizontal upper surface of a test bench and the vertical surface of a test sample.

Reference is now made to FIGS. 1-3 illustrating a new and improved hand-held stone impact simulator 10. As shown the stone impact simulator 10 includes a housing 12 that holds a projectile propulsion section, generally designated by reference numeral 14, and a projectile capture section, generally designated by reference numeral 16. As should be appreciated, the projectile propulsion section 14 functions to propel a projectile, such as a steel ball bearing, toward a test sample such as the windshield W. The projectile capture section 16 functions to capture the projectile after the projectile ricochets off the test sample/windshield W in a manner that dissipates energy and protects the simulator and projectiles from unnecessary wear and possible damage.

As illustrated, the housing 12 includes a support 18 at one end for engaging the test sample/windshield W. The projectile propulsion section 14 includes a regulated air feed 22 that is connected to a source of pressurized air (not shown). The projectile velocity is directly related to the applied pressure. Further, the projectile propulsion section 14 includes a feed tube 24 for feeding projectiles/ball bearings 26 from a supply chamber 27 into the charge modified Swagelok valve 34.

A single projectile/ball bearing 26 is released toward the test sample/windshield W through a barrel 30 by operation of the spring-loaded plunger 32 and modified Swagelok valve 34 that controls the flow of air received from the pressurized air source at the regulated air feed 22. More specifically, the modified Swagelok valve 34 receives a projectile/ball bearing 26 from the feed tube 24 and then is aligned with the barrel 30. One then depresses the plunger 32 against the force of the spring 33 in order to align the firing aperture 35 in the plunger with the modified Swagelok valve 34 and the barrel 30. The force of the pressurized air then drives the projectile/ball bearing 26 through the barrel 30 toward the test sample/windshield W.

As illustrated, a speed trap 36 may be provided between the end 38 of the barrel 30 and the test sample/windshield W. A speed trap 36 of substantially any appropriate design for the intended purpose may be utilized including, for example, one connected to a frequency meter 39 that converts the speed trap pulses to a mile-per-hour speed.

The projectile capture section 16 includes a rebound block 40, a spent projectile storage compartment 42 and a projectile energy dissipation element 44 provided between the rebound block and the spent projectile storage compartment.

The projectile energy dissipation element 44 includes a frustoconical wall 46. That frustoconical wall 46 has a cone angle of between 5 degrees and 20 degrees. In one particularly useful embodiment, the frustoconical wall has a cone angle of about 15 degrees. The significance of the cone angle of the frustoconical wall 46 will be described in detail below.

The rebound block 40 has an arcuate face 48. That arcuate face may have a radius of curvature between 1 and 3 inches. In one possible embodiment that arcuate face 48 has a radius of curvature of between 2.3 and 2.5 inches. In one particularly useful embodiment, that arcuate face 48 has a radius of curvature of about 2.41 inches.

The projectile capture section 16 further includes a curved ramp 50 between the rebound block 40 and the projectile energy dissipation element 44. The curved ramp 50 includes a shallow, arcuate channel 52. That arcuate channel may have a radius of curvature of between about 0.25 and about 0.50 inches. The arcuate channel assures that projectile will enter the projectile energy dissipation element 44 at the top.

As previously noted, in use the housing 12 of the stone impact simulator 10 is inclined at an angle of about 45 degrees with respect to the horizontal surface and the test sample/windshield W is oriented in a vertical plane (See FIG. 3). As should be further appreciated from reviewing the drawing figures, the barrel 30 and speed trap 36 are aligned along a first axis $A_1$. The rebound block 40, curved ramp 50, projectile energy dissipation element 44 and the spent projectile storage compartment 42 are aligned along a second axis $A_2$. The first axis $A_1$ is parallel to the second axis $A_2$. Further, the first and second axes $A_1$, $A_2$ are inclined at an angle of about 45 degrees with respect to a horizontal line.

In use, a projectile or ball bearing 26 is fired through the barrel 30 across the speed trap 36 into the face of the test sample/windshield W at an incident angle of about 45 degrees. The projectile/ball bearing 26 ricochets off of the test sample/windshield W into the arcuate face 48 of the rebound block 40. The angle can be between 10 to 75 degrees, and the required rebound radius will vary with the angle.

The projectile/ball bearing 26 bounces off of the arcuate face 48 of the rebound block 40 toward the curved ramp 50 which serves to redirect the projectile/ball bearing toward the upper portion of the frustoconical wall 46 of the projectile energy dissipation element 44. That wall is provided at a cone angle designed to bounce the projectile/ball bearing on the frustoconical wall 46 multiple times to dissipate the energy of the projectile/ball bearing and exit the lower section of the energy dissipation element 44. The projectile/ball bearing will finally be caught between the capture wall housing 42 and the lower wedge section of the curved ramp 50 without touching any other projectiles. The projectile/ball bearing will roll downwardly through the opening 54 in the projectile energy dissipation element 44 into the storage compartment. A plug 58 at the end of the storage compartment 42 may be removed in order to recover the spent projectiles/ball bearings 26 which may be inspected and reused if desired.

The projectile capture section 16 of the stone impact simulator 10 is specifically designed to successfully capture projectiles/ball bearings 26 that are fired by the projectile propulsion section 14 across a wide speed range such as 10 to 200 miles per hour. Significantly, the projectile energy dissipation element 44 of the projectile capture section 16 effectively dissipates the energy of those projectiles/ball bearings 26 before delivering the projectiles/ball bearings through the opening 54 into the spent projectile storage compartment 42. Thus, it should be appreciated that the spent projectiles are not engaged by a projectile/ball bearing 26 with any significant level of energy from the projectile propulsion section 14. Accordingly, the projectiles/ball bearings 26 are protected from projectile to projectile damage and the simulator 10 is protected from the potential wear and tear that would otherwise result from a projectile/ball bearing 26 with significant energy engaging/contacting other such projectiles/ball bearings.

The foregoing has been presented for purposes of illustration and description. It is not intended to be exhaustive or to limit the embodiments to the precise form disclosed. Obvious modifications and variations are possible in light of the above teachings. All such modifications and variations are within the scope of the appended claims when interpreted in accordance with the breadth to which they are fairly, legally and equitably entitled.

What is claimed:

1. A stone impact simulator, comprising:
   a projectile propulsion section to propel a projectile toward a test sample; and
   a projectile capture section to capture said projectile after ricocheting off of said test sample, said projectile capture section including a rebound block, a spent projectile storage compartment and a projectile energy dissipation element between said rebound block and said spent projectile storage compartment.

2. The stone impact simulator of claim 1, wherein said projectile energy dissipation element includes a frustoconical wall.

3. The stone impact simulator of claim 2, wherein said frustoconical wall has a cone angle of between 3 degrees and 20 degrees.

4. The stone impact simulator of claim 3, wherein said frustoconical wall has a cone angle of about 15 degrees.

5. The stone impact simulator of claim 2, wherein said rebound block has an arcuate face.

6. The stone impact simulator of claim 5, wherein said arcuate face has a radius of curvature of between 1 and 3 inches.

7. The stone impact simulator of claim 5, wherein said arcuate face has a radius of curvature of between 2.3 and 2.5 inches.

8. The stone impact simulator of claim 5, wherein said arcuate face has a radius of curvature of about 2.41 inches.

9. The stone impact simulator of claim 5, wherein said projectile capture section further includes a curved ramp between said rebound block and said projectile energy dissipation element.

10. The stone impact simulator of claim 9, wherein said curved ramp includes an arcuate channel.

11. The stone impact simulator of claim 10, wherein said arcuate channel has a radius of curvature of between 0.25 and 0.50.

12. The stone impact simulator of claim 9, wherein said projectile propulsion section includes a barrel to guide and accelerate said projectile toward said test sample.

13. The stone impact simulator of claim 12, further including a speed trap between said barrel and said test sample.

14. The stone impact simulator of claim 12, further including a housing for holding said projectile propulsion section and said projectile capture section.

15. The stone impact simulator of claim 14, wherein said housing includes a support for resting said housing against said test sample with said barrel at an angle of between about 10 to about 75 degrees with respect to said test sample.

16. The stone impact simulator of claim 15, wherein said housing is inclined at an angle of about 45 degrees with respect to a horizontal line and said test sample is oriented in a vertical plane.

17. The stone impact simulator of claim 13, wherein said barrel and said speed trap are aligned along a first axis.

18. The stone impact simulator of claim 17, wherein said rebound block, said curved ramp, said projectile energy dissipation element and said spent projectile storage compartment are aligned along a second axis.

19. The stone impact simulator of claim 18, wherein said first axis and said second axis are parallel.

20. The stone impact simulator of claim 19, wherein said first axis and said second axis are inclined at an angle of between about 10 and about 75 degrees with respect to a horizontal line.

* * * * *